United States Patent
Leiblein et al.

(10) Patent No.: US 8,620,049 B2
(45) Date of Patent: Dec. 31, 2013

(54) INTERVENTIONAL ROADMAP METHOD WITH OPTIMIZATION OF THE MASK PHASE

(75) Inventors: Rudolf Leiblein, Weisendorf (DE); Martin Spahn, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 843 days.

(21) Appl. No.: 12/821,344

(22) Filed: Jun. 23, 2010

(65) Prior Publication Data
US 2010/0329516 A1 Dec. 30, 2010

(30) Foreign Application Priority Data
Jun. 30, 2009 (DE) .................. 10 2009 031 162

(51) Int. Cl.
*G06K 9/00* (2006.01)
*G06K 9/40* (2006.01)

(52) U.S. Cl.
USPC .......................................... 382/130; 382/181

(58) Field of Classification Search
USPC ................................ 382/130, 181; 378/98.12
See application file for complete search history.

(56) References Cited

U.S. PATENT DOCUMENTS

| | | | |
|---|---|---|---|
| 2006/0269134 A1* | 11/2006 | Wang et al. | 382/181 |
| 2008/0240363 A1 | 10/2008 | Grebner et al. | |
| 2010/0172474 A1* | 7/2010 | Vogt et al. | 378/98.12 |

FOREIGN PATENT DOCUMENTS

DE    102005012700 A1    9/2006

* cited by examiner

*Primary Examiner* — Luke Gilligan

(57) ABSTRACT

An interventional roadmap method with optimization of the mask face is proposed. At least two empty images and at least two fill images are recorded in a mask phase A with a matrix-type array of pixels and stored. The empty and fill images are processed such that the gray values of each pixel of the x-ray images from mask phase A are arranged in ascending order. A mask image is computed from the processed empty and fill images such that the smallest gray values are averaged and from which the mask image will be formed. At least one current x-ray image is recorded and subtracted from the mask image to create roadmap images.

10 Claims, 3 Drawing Sheets

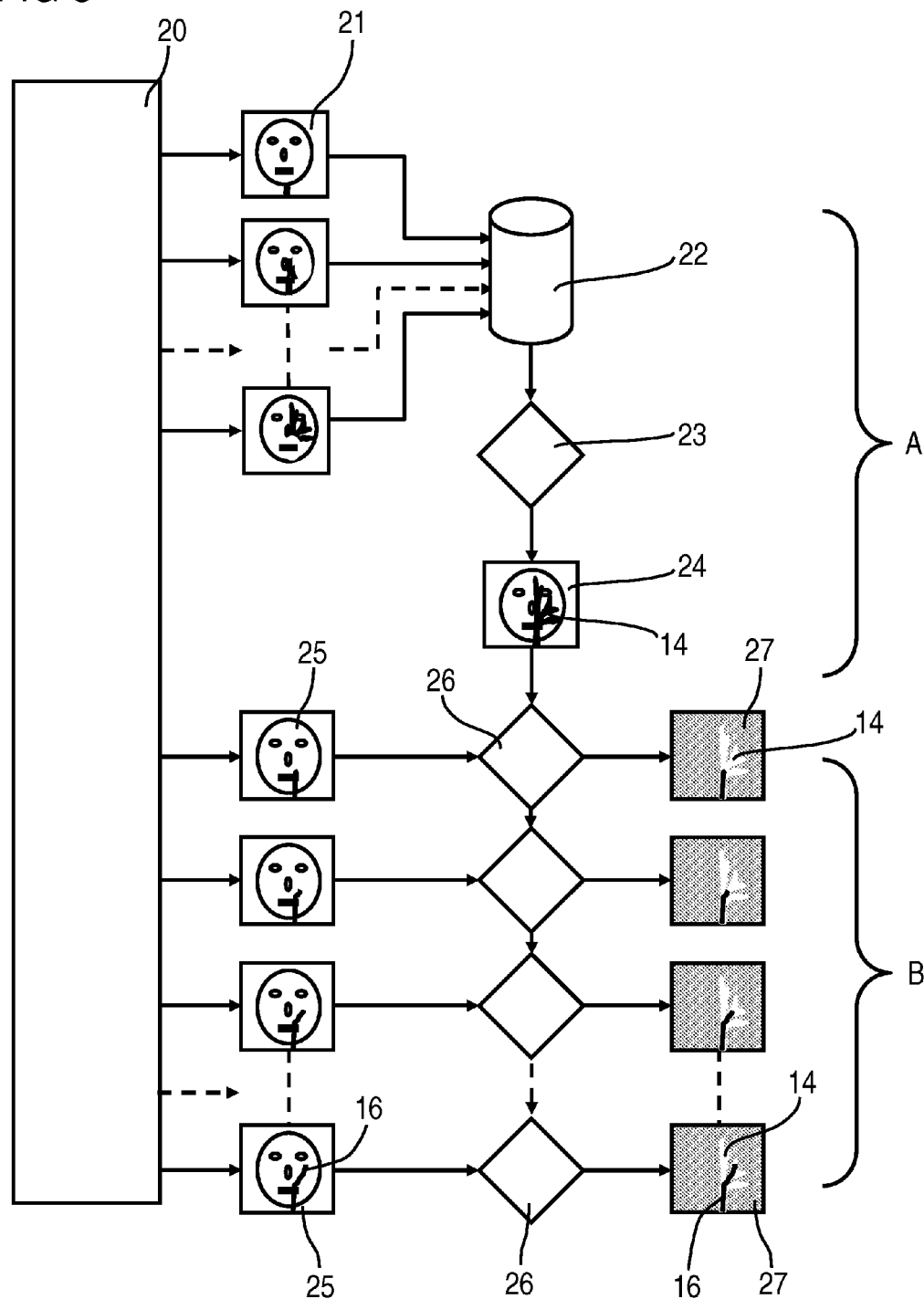

INTERVENTIONAL ROADMAP METHOD WITH OPTIMIZATION OF THE MASK PHASE

CROSS REFERENCE TO RELATED APPLICATIONS

This application claims priority of German application No. 10 2009 031 162.9 filed Jun. 30, 2009, which is incorporated by reference herein in its entirety.

FIELD OF THE INVENTION

The invention relates to an interventional roadmap method in which, in a first phase, first x-ray images are recorded with pure anatomy during the system dose regulation phase and then x-ray images are recorded during the fill phase (vessel is filled with contrast medium), from which the mask image is produced. In a "working" or "intervention" phase x-ray images are produced using fluoroscopy while a wire, a catheter, a coil or another object is being moved in the vessel. Roadmap images are produced by subtraction and where necessary further image processing.

BACKGROUND OF THE INVENTION

For diagnostic examination and for interventional procedures, e.g. in cardiology, radiology and also neuro-surgery, interventional x-ray systems are used for imaging, the typical major features of which can be for example be a robot-controlled C-arm to which an x-ray tube and an x-ray detector are attached, a patient support table, a high-voltage generator for generating the tube voltages, a system control unit and a display system including at least one monitor. This type of C-arm x-ray system, which is shown by way of example in FIG. 1, typically features a C-arm 2 supported rotatably on a stand in the form of a six-axis industrial or articulated-arm robot 1, attached to the ends of which are an x-ray source, for example an x-ray tube unit 3 with x-ray tubes and collimators, and an x-ray image detector 4 as an imaging unit.

By means of the articulated-arm robot 1 known for example from DE 10 2005 012 700 A1, which preferably has six axes of rotation and thereby 6 degrees of freedom, the C-arm 2 can be adjusted spatially as required, for example by being turned around the center of rotation between the x-ray tube unit 3 and the x-ray detector 4. The inventive x-ray system 1 to 4 is especially able to be rotated around centers of rotation and axes of rotation in the C-arm plane of the x-ray image detector 4, preferably around a center point of the x-ray image detector 4 and around the center point of the axes of rotation intersecting with the x-ray image detector 4.

The known articulated-arm robot 1 has a base support which is mounted fixed on a floor for example. A carousel able to be rotated around a first axis of rotation is attached rotatably thereto. Attached to the carousel pivotably around a second axis of rotation is a robot motion link to which a robot arm is attached rotatably around a third axis of rotation. A robot hand is attached at the end of the robot arm rotatably around the fourth axis of rotation. The robot hand has an attachment element for the C-arm 2 which is able to be pivoted around a fifth axis of rotation and is rotatable around a sixth axis of rotation running at right angles thereto.

The realization of the x-ray diagnostic device is not dependent on industrial robots Normal C-arm devices can also be used.

The x-ray image detector 4 can be a rectangular or square, flat semiconductor detector which is preferably made of amorphous silicon (a-Si). Integrating and possibly scanning CMOS detectors can also be used.

Located as an examination object on a patient support table 5 in the beam path of the x-ray tube unit 3, for recording an image of a heart for example, is a patient 6 to be examined. Connected to the x-ray diagnostic device is a system control unit 7 with an image system 8 which receives and processes the image signals of the x-ray image detector 4 (control elements are typically not shown). The x-ray images can then be viewed on a monitor 9.

An important method of interventional radiology is the so-called roadmap method. In this method, as is explained with reference to FIG. 2, in a mask phase A, a mask image 13 is initially created which contains the contrast medium-filled vascular tree 14. In such cases one or more x-ray images are recorded which produce x-ray images without filling, so-called empty images 10. Subsequently further x-ray images are detected after contrast media have been injected, so-called fill images 11.

The mask image 13 is determined by means of a mask computation from the empty 10 and fill images 11 12 as mask M(i,j). Usually the various x-ray images ($B_k(i,j)$ k=1,K) are averaged using fluoroscopic, i.e. small, doses. The known moving weighted averaging can be used for this purpose, in which a percentage of the previous image is overlaid with the current image—possibly coupled to a movement detector.

If necessary, for improved display of the vascular tree 14, an "opacity" method is used, i.e. the respective darkest value of a pixel from all x-ray images is used in the mask image 13. The image frequency is usually the same as during the roadmap phase B, in which the mask image 13 is subtracted from a fluoroscopy image 15 $B_l$ l=1,L in which an object, typically a wire, a catheter 16 or a "coil" is moved in a vessel of the vascular tree 14. Through this subtraction 17 all anatomical (immobile) structures are subtracted and the filled vascular tree 14—now shown in "white" by the subtraction—and the catheter 16 are left. This greatly reduces the image contrast and vascular tree 14 and catheter 16 are sensibly visible in roadmap images 19 $RM_l(i,j)$, l=1,L. In mask phase A no contrast medium is added but the anatomy is simply recorded. In the roadmap phase B adhesives are then introduced by means of a catheter 16 at the point to be embolized. The course of the adhesive is followed in this roadmap phase B. By subtraction 17 of the mask image 13 which only contains the anatomy from the image series 15 with adhesives and the anatomy and if necessary subsequent image processing 18, only the adhesive remains, the course of which can now be shown in very high contrast in roadmap images 19 $RM_l(i,j)$, l=1,L.

The previous method has a few disadvantages:
  The generation of the mask image (mask phase A) takes up to two seconds. This depends amongst other things on the image rate and the image post processing steps (such as the averaging method). The user (generally the radiologist) would like however, especially for embolizations, to see practically instantly how strongly the adhesive is running or whether it has already begun to harden and is no longer running.
  The averaging method (moving weighted average) reduces the maximum possible contrast of the contrast medium during the mask phase A in the smallest vessels (where the contrast medium only arrives during the last recordings within the series of x-ray image 10 and 11).

SUMMARY OF THE INVENTION

The object of the invention is to embody a method of the type mentioned at the start such that the roadmap method either achieves better contrast and an improved signal-to-noise ratio through improved averaging and opacity methods or also allows an improved timing behavior and thereby a faster creation of the mask image.

The object is inventively achieved by the features specified in the independent claims. Advantageous embodiments are specified in the dependent claims.

In the above-mentioned method this is achieved through the following steps:
a) Recording of at least two empty images in a mask phase A with a matrix-type array of pixels,
b) Recording of at least two fill images in mask phase A with a matrix-type array of pixels,
c) Storage of the individual empty and fill images,
d) Processing of the empty and fill images such that the gray values of each pixel of the x-ray images from mask phase A are arranged in ascending order,
e) Computing a mask image from the processed empty and fill images such that the smallest gray values are averaged from which the mask image will be formed,
f) Detecting at least one current x-ray image (fluoroscopy image),
g) Subtracting (18, 26) the least one current x-ray image (15, 25) from the mask image (13, 24) for creation of roadmap images (19, 27) and
h) Reproducing the roadmap images (19, 27).

In the roadmap method improved in this way all x-ray images are first stored in the mask phase. The mask image is computed from these. During the mask phase all other parameters for activation of generator and x-ray image detector may be selected (e.g. dose, image frequency) as in the subsequent roadmap phase. In the roadmap phase each x-ray image is processed with the mask image into a roadmap image. If necessary information from a previous image (previous images) is also used.

Advantageously the processing of the individual empty and fill images in accordance with step d), can include the gray values of each pixel of x-ray images from the mask phase being arranged in ascending order.

It has proved advantageous for the computation of a mask image from the processed empty and fill images in accordance with step e) to include the smallest (darkest) gray values from which the mask image $M(i,j)=1/N\Sigma G'_{ij}(n)$ is formed, being averaged.

Inventively the value for each pixel can be selected independently or defined for each pixel by the typical gray value.

Step f) can inventively include the detection of an object.

In an advantageous manner a further step can be provided between step f) and g) in which the mask image is subjected to further image processing steps.

Inventively the contrast, the image sharpening or the noise reduction can be improved in a further step.

It has proved advantageous for the processing of the individual empty and fill images in accordance with step d) to further include the standard deviation of each gray value array being formed for each pixel, for expected noise to be determined at each point of the image, for it to be determined in accordance with a metric (plausibility), by comparing the standard deviation and the noise to be expected whether contrast media has been applied in the corresponding pixel, for a local contrast enhancement to be carried out as follows:

$$M'(i,j)=c_1*M(i,j), \text{ if } S(i,j)>c_2*R(i,j)$$

$$M'(i,j)=M(i,j), \text{ if } S(i,j)<=c_2*R(i,j)$$

with for a gray value less than $c_1=1.0$, all pixels at which contrast media was determined becoming even darker, all other pixels not being changed, or for $c_2$ greater than 1.0, a noise limiting being performed.

In an advantageous manner the noise to be expected can be determined by measurements from a number of x-ray images, in which no contrast medium has yet been added, and/or can be determined from the gray values of an individual native image.

BRIEF DESCRIPTION OF THE DRAWINGS

The invention is explained in greater detail below with reference to exemplary embodiments shown in the drawing. The figures show.

DETAILED DESCRIPTION OF THE INVENTION

Figure 1:
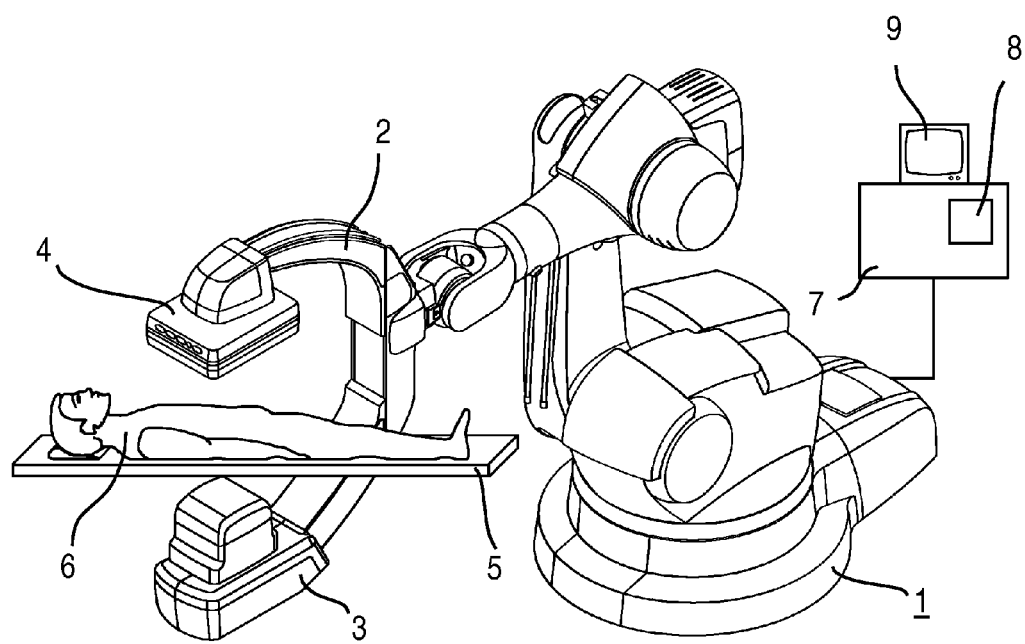
FIG. 1 a known x-ray C-arm system for radiology, cardiology or neuro-surgery with an industrial robot as its support device, FIG. 2 a principle of the previously usual roadmap method with mask phase A (mask formation) and roadmap phase B (working phase) (state-of-the-art) and FIG. 3 a flow diagram of the inventive roadmap method.

FIG. 3 shows the typical sequence of the inventively optimized x-ray method. During mask phase A, in which contrast media is generally injected into the vascular tree, x-ray images $B_k$ are recorded and initially stored. The mask image M is computed from the stored x-ray images $B_k$. During mask phase A specific generator parameters and detector parameters, such as image frequency, dose, tube focus, are used. In roadmap phase B—possibly with changed system parameters generator, x-ray detector—further x-ray images $B_l$ are recorded and processed with the mask image M into roadmap images $R_l$.

With an image-synchronous brightness control, for example by compensating for generator fluctuations, the mask phase can begin even from the first x-ray image.

The inventive method will now be explained in greater detail with reference to FIG. 3. X-ray images 21 of the mask phase A, which consist of empty images 10 and fill images 11, are created by the x-ray system 20 with system control 7, high-voltage generator, x-ray tube unit 3 and x-ray image detector 4. These x-ray images 21 are all stored individually in a data memory 22. In the further course of the mask phase A the individual x-ray images 21 are called up from the data memory 22 and a mask image 24 is created by image processing 23, in which the complete vascular tree 14 with the anatomy, typically the bones, is to be seen.

In a roadmap phase B x-ray images 25 are created by the x-ray system 20 and supplied one after another to an image processor 26 one of the functions of which is to reproduce by means of negative overlaying roadmap images 27 on the monitor 9, in which the vascular tree 14 as a roadmap and the introduced catheter 16 are to be seen.

Figure 2:
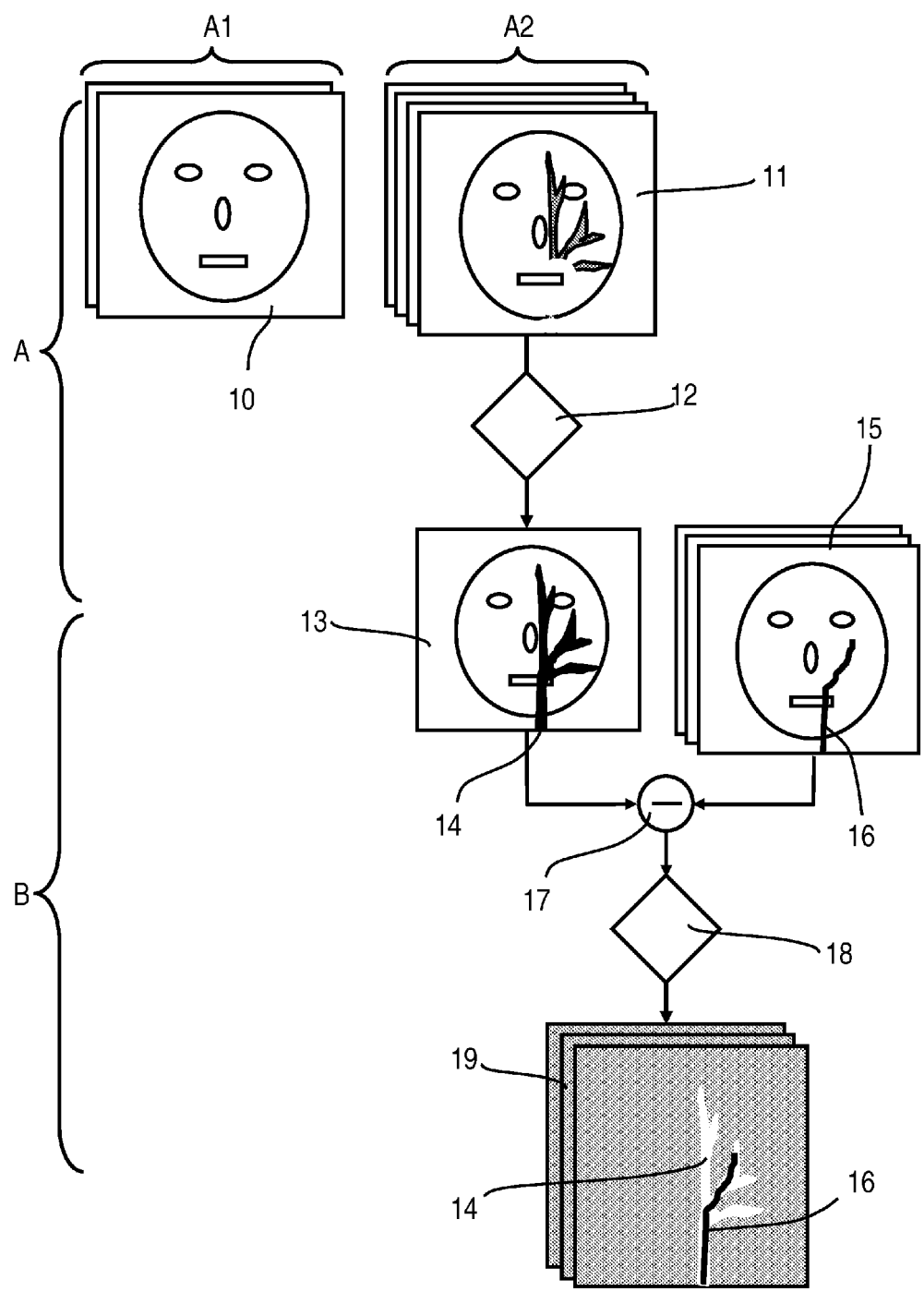

The disadvantages of the known roadmap method described with reference to FIG. 2 can be improved or bypassed with the aid of a few partly inventively combinable methods which are to be seen in conjunction with FIG. 3 for example, which either achieve a better contrast and improved noise behavior by means of improved averaging and opacity methods or will also allow an improved timing behavior and thereby a faster creation of the mask image.

Improved Averaging and Opacity Method
The following steps are to be executed:
Instead of a moving average method in which only the current x-ray image is computed with the last x-ray image, all x-ray images 21 $Bk(i,j)$ $k=1,K$ are first stored during mask phase A.

Subsequently the gray values Gij(k) of each pixel i,j of the x-ray images 21 Bk(i,j) k=1,K from mask phase A are arranged in ascending order. For each pixel an ordered array of grey values G'ij(k), k=1,K is produced. By this method the temporal course of the contrast medium in the vascular tree is decorrelated and the pixels at a given point in time in which the contrast medium was present at its strongest will lie at the bottom end of the ordered array.

As the next step the mask image 24 is created. The smallest (darkest) N (with N<=K) grey values G'ij(n), n=1,N are averaged and a mask image 24 M is produced $$M(i,j) = 1/N \Sigma G'_{ij}(n)$$

This method ensures that the maximum contrasts of the vessel filled at different times (lowest grade values) are stored in the mask image 24 M(i,j). In addition this method leads to a noise minimization since the mask values are entered with a "bias"—in this case always the lowest values. The value N can be selected between 1 and maximum K (requirement K>=1). In practice this might depend on the selected dose of the x-ray images 21 in the mask phase A.

In addition even the value N for each pixel could be selected independently (N ij), e.g. determined by the typical gray value G'ij(n=1), since depending on the position in the image through the anatomy, more out less radiation falls on the x-ray image detector 4 and thereby the local noise is also different.

The mask image 24 M(i,j) can be subjected to further image processing steps for improving the contrast, image sharpening or noise reduction.

For the specific case N=1, i.e. when only the smallest (darkest) gray values of each pixel sorted from the K x-ray images in mask phase A into the Mask image and no averaging is to be applied, the K x-ray images do not first have to be stored but the analysis can be realized "on-the-fly". In this case the first image from a mask phase A, possibly after synchronizing the dose regulation, is stored as mask image 24. In each further x-ray image 21 in the mask phase A the great value of one pixel i,j is then replaced in the mask image 24 if it is darker than the grey value already contained there.

This method can be improved by a local contrast enhancement precisely where contrast medium will be "measured". To this end the standard deviation S (i,j)=σ(Gij) of each gray value array Gij(k) k=1,K is formed for each pixel i,j. In addition the noise R(i,j) to be expected at each location of the image is determined. This can fluctuate from place to place through local dose variation—caused by more or less local absorption. The noise R(i,j) can be determined by measurement, for example in a number of x-ray images 21, in which no contrast means has yet been added. As an alternative the noise R(i,j) can be determined from the gray values of an individual native image, since then a first approximation and for sufficiently high doses the noise is proportional to the square root of the signal. It is now determined by comparison of S(i,j,) and R(i,j) in accordance with the metric (plausibility) whether contrast media has been applied in the corresponding pixel i,j. In general the standard deviation S(i,j) is somewhat greater than the noise R(i,j). The local contrast enhancement of the mask image M(i,j) is then typically ensured as follows:

$$M'(i,j) = c_1 * M(i,j), \text{ falls } S(i,j) > c_2 * R(i,j)$$

$$M'(i,j) = M(i,j), \text{ if } S(i,j) <= c_2 * R(i,j).$$

In this case for example $c_1=0.8$ and $c_2=2.0$. For a value less than $c_1=1.0$ all pixels at which contrast medium was determined become darker, all other pixels are not picked up. With $c_2$ greater than 1.0 the limitation of noise is undertaken.

During the working phase or interventional roadmap phase B the mask image 24 M(i,j) (or M'(i,j)) is then subtracted from further x-ray images Bl(i,j) l=1, L and is subjected to further image processing steps if necessary. The roadmap images RMl(i,j) l=1, L produced. See also FIG. 3 for the sequence.

If, instead of the normal contrast media which creates a higher x-ray contrast, i.e. darker gray values, than blood, such as for example $CO_2$, the blood is forced out and thus a brighter contrast created, the mask computation must be adapted accordingly.

This new mask method can execute approximately, without demanding the previous storage of all x-ray images Bk(i,j) k=1,K. One could also flag the respective N smallest pixel values in order to also determine the mask image M and also the standard deviation S in an approximation "on the fly". The noise R could be determined by using reverse computation from the signal values of any of the x-ray images B (and use of calibration data to determine the proportionality factor between noise and signal independently of aspects such as tube voltage and detector mode).

Improved Timing Behavior (Fastest Possible Mask Creation):

Higher image frequency during the mask phase a than in the "working phase" or roadmap phase B. If for example the image frequency in the roadmap phase B is 4 or 7.5 fps (frames per second) it can be increased in the mask phase A to 15 or 30 fps. This especially enables the control process of the x-ray system to be optimized before injection of the contrast medium into the vascular tree during the first x-ray images 10, 21. This is also helps to improve the noise behavior however, since the averaging over more available x-ray images 10, 11, 21 reduces the noise.

Increasing the dose in the mask phase A without enhancing the kV plateau (a kV increase because of the skin dose rule would generally have a negative effect on the contrast of the mask image).

This could be achieved by maximizing the tube current and the pulse length while retaining the desired tube voltage kV. This can however under some circumstances require the lifting of the 10 or 20 R/min skin dose rule. However this can be justified by an improved image quality and thereby faster conclusion of the intervention, without an increased dose having to be applied overall. Possibly a limiter would have to be built in to prevent too high a dose exceeding the dynamic range of the x-ray image detector 4.

The dose increase can possibly also be accompanied by the choice of another, for example greater tube focus.

If detector-internal modes are switched between mask phase A and roadmap phase B it can be advantageous, after mask phase A, i.e. after detector mode switchover and still before roadmap phase B, to acquire one or more x-ray images 10, 21 in the new detector mode. This occurs without radiation in order to suppress possible mode switchover artifacts which could lead to image disruptions. Only then is the roadmap phase B started.

Through the inventive embodiment of the roadmap method in which in mask phase A all x-ray images are first stored and from these the mask image is calculated as well as in roadmap phase B each x-ray image B is processed with the mask image into a roadmap image R, either through an improved averaging and opacity methods a better contrast and improved noise behavior and/or an improved timing behavior and thereby a faster creation of the mask image can be achieved.

The invention claimed is:

1. A method for creating interventional roadmap images, comprising:
   recording at least two empty images in a mask phase with a matrix-type array of pixels by an x-ray system;
   recording at least two fill images in the mask phase with a matrix-type array of pixels by the x-ray device;
   storing the empty and fill images in an image processing system;
   arranging gray values of each pixel of the empty and fill images in ascending order by the image processing system;
   averaging smallest gray values from the empty and fill images to form a mask image by the image processing system;
   recording at least one current image by the x-ray system;
   subtracting the at least one current image from the mask image to create roadmap images by the image processing system; and
   displaying the roadmap images on a monitor,
   wherein the smallest gray values $G'_{ij}(n)$, $n=1, N \leq K$ is averaged to form the mask image
   $$M(i,j) = 1/N \Sigma G'_{ij}(n).$$

2. The method as claimed in claim 1, wherein the gray values $G_{ij}(k)$ of each pixel i,j of the empty and fill images $B_k(i,j)$, $k=1,K$ from the mask phase is arranged in ascending order.

3. The method as claimed in claim 1, wherein the value N is selected independently for each pixel $N_{ij}$.

4. The method as claimed in claim 1, wherein the value N is determined for each pixel by a gray value $G'_{ij}(n=1)$.

5. The method as claimed in claim 1, wherein the at least one current image detects an object.

6. The method as claimed in claim 1, wherein the mask image $M(i,j)$ is further processed before being subtracted by the at least one current image.

7. The method as claimed in claim 6, wherein the mask image $M(i,j)$ is further processed for improving contrast, image sharpening and/or noise reduction.

8. The method as claimed in claim 1, wherein:
   a standard deviation $S(i,j) = \sigma(G_{ij})$ for each pixel i,j is calculated for each gray value array $G_{ij}(k)$ $k=1,K$,
   a noise $R(i,j)$ at each location of the empty and fill images is determined,
   the standard deviation $S(i,j)$ is compared with the noise $R(i,j)$ in accordance with a metric to determine whether a contrast medium has been applied in a corresponding pixel i,j, and
   a local contrast enhancement of the mask image $M(i,j)$ is carried out as follows:
   $$M'(i,j) = c_1 * M(i,j), \text{ if } S(i,j) > c_2 * R(i,j)$$
   $$M'(i,j) = M(i,j), \text{ if } S(i,j) <= c_2 * R(i,j)$$
   with:
   for a gray value of less than $c_1$ equals 1.0, pixels at which the contrast medium has been applied become darker, all other pixels are not changed, or for $c_2$ greater than 1.0, the noise is limited.

9. The method as claimed in claim 8, wherein the noise $R(i,j)$ is determined by measuring a number of the empty and fill images in which no contrast medium has been applied.

10. The method as claimed in claim 8, wherein the noise $R(i,j)$ is determined from the gray values of the empty and fill images.

* * * * *